US009459468B2

United States Patent
Wietschorke (10) Patent No.: US 9,459,468 B2
(45) Date of Patent: Oct. 4, 2016

(54) METHOD OF MAKING A SPECTACLE LENS PROVIDING AN ASTIGMATIC CORRECTION AND SPECTACLES INCLUDING SAID SPECTACLE LENS

(71) Applicant: Carl Zeiss Vision International GmbH, Aalen (DE)

(72) Inventor: Helmut Wietschorke, Aalen (DE)

(73) Assignee: Carl Zeiss Vision International GmbH, Aalen (DE)

( * ) Notice: Subject to any disclaimer, the term of this patent is extended or adjusted under 35 U.S.C. 154(b) by 0 days.

(21) Appl. No.: 13/901,270

(22) Filed: May 23, 2013

(65) Prior Publication Data
US 2013/0314666 A1   Nov. 28, 2013

(30) Foreign Application Priority Data
May 23, 2012   (DE) .................. 10 2012 010 221

(51) Int. Cl.
*G02C 7/02*       (2006.01)
*G02C 7/06*       (2006.01)
*A61B 3/103*     (2006.01)

(52) U.S. Cl.
CPC ............... *G02C 7/027* (2013.01); *G02C 7/02* (2013.01); *G02C 7/024* (2013.01); *G02C 7/025* (2013.01); *G02C 7/028* (2013.01); *G02C 7/061* (2013.01); *A61B 3/1035* (2013.01)

(58) Field of Classification Search
CPC ......... G02C 7/00; G02C 7/024; G02C 7/025
USPC ......... 351/159.73–159.76, 159.52, 216, 246, 351/236, 200, 159.01, 159.06, 159.07
See application file for complete search history.

(56) References Cited

U.S. PATENT DOCUMENTS 4,613,217 A   9/1986 Fuerter et al.
4,787,733 A   11/1988 Silva
(Continued)

FOREIGN PATENT DOCUMENTS

EP        1 154 302 A1    11/2001
WO           01/92948 A1   12/2001
WO    WO 2012/046230   *   4/2012  .............. A61B 3/00

OTHER PUBLICATIONS

Extended search report of the European Patent Office dated Aug. 12, 2013 in corresponding European patent application 13002665.1.
(Continued)

*Primary Examiner* — Bumsuk Won
*Assistant Examiner* — William R Alexander
(74) *Attorney, Agent, or Firm* — Walter Ottesen, P.A.

(57) ABSTRACT

A method of making a spectacle lens providing at least an astigmatic correction includes measuring a direction of an axis of an astigmatism of an eye for each of three different directions of gaze of the eye. Thereafter, a position of the spectacle lens is determined relative to the eye. A shape of a surface of the spectacle lens is computed based on the determined position of the spectacle lens relative to the eye and the at least three measured directions of the axis of the astigmatism. A primary orientation of the eye is determined based on the three measured directions of the axis of the astigmatism. The shape of the surface of the spectacle lens is calculated based on the determined position of the spectacle lens relative to the eye and by applying Listing's Law based on the determined primary orientation of the eye.

31 Claims, 2 Drawing Sheets

(56) References Cited

U.S. PATENT DOCUMENTS

| | | | |
|---|---|---|---|
| 5,576,780 A * | 11/1996 | Yancey | A61B 3/103 351/209 |
| 6,012,813 A | 1/2000 | Qi | |
| 6,142,625 A | 11/2000 | Sawano et al. | |
| 6,318,859 B1 | 11/2001 | Baudart et al. | |
| 6,382,789 B1 | 5/2002 | Baudart et al. | |
| 8,998,409 B2 | 4/2015 | Altheimer et al. | |
| 2003/0174278 A1 | 9/2003 | Esser et al. | |
| 2004/0032565 A1 * | 2/2004 | Yamakaji et al. | 351/177 |
| 2006/0055877 A1 | 3/2006 | Yanari | |
| 2006/0176446 A1 | 8/2006 | Kaga | |
| 2007/0159601 A1 * | 7/2007 | Ho | G02C 7/047 351/221 |
| 2010/0149484 A1 | 6/2010 | Berthezene et al. | |
| 2011/0202286 A1 * | 8/2011 | De Rossi | G02C 7/02 702/19 |
| 2011/0262519 A1 * | 10/2011 | Franklin | B29D 11/00134 424/429 |
| 2012/0002161 A1 | 1/2012 | Altheimer et al. | |
| 2012/0016644 A1 * | 1/2012 | De Rossi | G02C 7/02 703/2 |
| 2012/0033179 A1 | 2/2012 | Kratzer et al. | |
| 2013/0188143 A1 * | 7/2013 | Carmon et al. | 351/216 |

OTHER PUBLICATIONS

Stephenson, P., "Spectacle lenses designed for the modified Listing eye rotation", J. Opt. A: Pure Appl. Opt. 6 (2004), pp. 246 to 252, IOP Publishing Ltd., UK.

English translation and Office action of the German Patent Office dated Jul. 17, 2012 in German patent application 10 2012 010 221.5 on which the claim of priority is based.

Porrill, J. et al, "The variation of torsion with vergence and elevation", Vision Research 39 (1999), pp. 3934 to 3950, Elsevier Science Ltd.

English translation and Office action of the Chinese Patent Office dated Dec. 23, 2015 in corresponding Chinese patent application 201310304027.5.

* cited by examiner

METHOD OF MAKING A SPECTACLE LENS PROVIDING AN ASTIGMATIC CORRECTION AND SPECTACLES INCLUDING SAID SPECTACLE LENS

CROSS REFERENCE TO RELATED APPLICATION

This application claims priority of German patent application no. 10 2012 010 221.6, filed May 23, 2012, the entire contents of which are incorporated by reference herein.

FIELD OF THE INVENTION

The invention relates to methods of making spectacle lenses providing at least an astigmatic correction, and to spectacles including such spectacle lenses.

BACKGROUND OF THE INVENTION

Spectacle lenses are usually manufactured according to a prescription of an ophthalmologist or an optician. The ophthalmologist or optician, respectively, determines the ametropia of an eye of a customer and determines a prescription of a spectacle lens for the eye such that, when a spectacle including the lens is worn by the customer, the ametropia of the eye is compensated as far as possible. The prescription typically comprises values for a spherical effect and, if necessary, values for the astigmatic effect of the spectacle lens, wherein the astigmatic effect is defined by a cylindrical power and a direction of the axis of the astigmatism. The prescription may further comprise additional values, such as a prismatic power, an addition, which defines a difference between spherical powers at a near reference point and a distance reference point of a multifocal lens, or an interocular distance.

The prescription includes values of the astigmatic effect if the eye of the customer requires an astigmatic correction. The spectacle lens is then manufactured such that it provides the astigmatic effect at at least one reference point by providing a corresponding cylindrical power and direction of axis. A spectacle lens should compensate the astigmatism of the eye not only at one reference point but, if possible, across the whole surface of the spectacle lens.

The most simple way of correcting an astigmatism is to provide a surface of a spectacle lens with a toric shape such that the astigmatism of the eye is sufficiently corrected at least at a reference point or a region around this reference point.

It has been found that such correction of an astigmatism does not provide completely satisfying results for customers and, in particular, those customers requiring an astigmatic correction of more than 1 or 2 diopters.

SUMMARY OF THE INVENTION

Accordingly, it is an object of the present invention to provide a method of making a spectacle lens allowing for improved correction of an astigmatism.

According to embodiments of the invention, a method of manufacturing of a spectacle lens providing at least an astigmatic correction comprises measuring a direction of an axis of an astigmatism of an eye for each of at least three different directions of gaze of the eye; determining a position of the spectacle lens relative to the eye; and computing a shape of a surface of the spectacle lens based on the determined position of the spectacle lens relative to the eye and the at least three measured directions of the axis of the astigmatism.

The inventor has found that the human eye rotates within the eye socket in a specific way when the eye is not in a same position as it was when the astigmatism was measured. When the eye rotates from a reference position upwards and to the right or downwards and to the left, the direction of the axis of the astigmatism will also rotate, such that the astigmatism will not be fully corrected by a pure toric lens surface in which the orientations of the principle meridians do not change across the surface.

A solution can be achieved by designing the spectacle lens such that bundles of light rays which traverse the spectacle lens for different directions of gaze experience axis directions of the astigmatic effect corresponding to those axis directions of the astigmatism of the eye which are required at the different directions of gaze.

According to some embodiments herein, the measuring of the direction of the axis of the astigmatism of the eye is performed for more than 15 and in particular for more than 30 or more than 60 different directions of gaze, wherein the calculating of the shape of the surface of the spectacle lens includes a simulation of light rays traversing the eye and the spectacle lens for a plurality of different directions of gaze of the eye, and wherein the direction of the astigmatism of the eye for the plurality of different directions of gaze is determined by interpolation of the measured directions of the axis. Herein, the position of the spectacle lens relative to the eye can be taken into consideration.

According to other embodiments herein, the method further comprises determining a primary orientation of the eye based on the at least three measured directions of the axis of the astigmatism, wherein the shape of the surface of the spectacle lens is calculated based on the determined position of the spectacle lens relative to the eye and by applying Listing's Law based on the determined primary orientation of the eye.

Listing's Law states that all achieved eye orientations can be reached by starting from one specific "primary" reference orientation and then rotating about an axis that lies within the plane orthogonal to the primary orientation's gaze direction (line of sight/visual axis). This plane is called Listing's plane. This definition implies that, if we start from any chosen eye orientation, all achieved eye orientations can be reached by starting from this orientation and then rotating about an axis that lies within a specific plane that is associated with this chosen orientation. As a consequence, only for the primary reference orientation is the gaze direction orthogonal to its associated plane.

In the context of applying Listing's Law, the inventor has further found that the primary orientation is not predetermined by an arbitrary orientation, such as achieved when viewing in the major visual direction which is mainly assumed for visual purposes when viewing through a centration marking of a progressive lens. Moreover, it has been found that the primary orientation according to Listing's Law differs between customers. Therefore, it is advantageous to determine the primary orientation according to Listing's Law for each customer by performing measurements on the customer. For this purpose, the direction of the axis of the astigmatism of the eye is measured for at least three different directions of gaze. The measured at least three different directions of the axis of the astigmatism allow to determine the primary orientation of the eye by applying Listing's Law. As soon as the primary orientation of the eye is known, the direction of the axis of the astigmatism can be determined for all possible directions of gaze by applying Listing's Law. It is then possible to calculate the astigmatic powers of the spectacle lens for all possible directions of gaze such that the astigmatism is sufficiently compensated for all directions of gaze. The bundles of light rays contributing to image formation in the eye at a given direction of gaze traverse only a portion of the spectacle lens, and different portions of the spectacle lens are traversed when viewing in different directions. Therefore, the different portions of the spectacle lens may provide different astigmatic powers such that the astigmatism of the eye is compensated for different directions of gaze. Different astigmatic powers can be provided by different portions of the spectacle lens, for example, by designing one or both surfaces of the spectacle lens such that they deviate from the pure toric shape. Such surfaces are free-form surface in that sense that their shapes do not have a simple symmetry, such as the symmetry of a spheric surface or of a toric surface.

According to further embodiments, the calculating of the shape of the surface of the spectacle lens includes a simulation of light rays traversing the eye and the spectacle lens for a plurality of different directions of gaze of the eye, and wherein, in the simulation, directions of the axis of the astigmatism of the eye are calculated for the plurality of directions of gaze by applying Listing's Law based on the determined primary orientation.

According to exemplary embodiments herein, at least two of the at least three different directions of gaze differ by more than 25° or by more than 35° in a vertical direction relative to the eye, and/or at least two of the at least three different directions of gaze differ by more than 25° or by more than 35° in a horizontal direction relative to the eye. These relatively large differences between the different directions of gaze at which the measurements are performed may result in an increased numerical stability of the data processing in the subsequent analysis of the measurement data, resulting in an improved accuracy of the final result.

According to further exemplary embodiments herein, at least one of the at least three directions of gaze is achieved by a combination of a horizontal eye movement and a vertical eye movement of more than ±10° relative to the orientation of the eye in straight horizontal direction of gaze or the major visual direction. This can be achieved, for example, when at least two of the at least three directions of gaze are situated in an azimuthal direction about a straight direction of gaze outside of an angular range of ±10° from a vertical direction and outside of an angular range of ±10° from a horizontal direction. This is the case, for example, if at least two of the three different directions of gaze have an azimuthal angle outside of an angular range of ±10° about the vertical direction and outside of an angular range of ±10° about the horizontal direction. This corresponds to directions of gaze located within ranges from 10° to 80°, from 100° to 170°, from 190° to 260° or from 280° to 350° in the TaBo-Diagram, wherein the TaBo-Diagram is the semicircular diagram of angles from 1° to 180°, starting from the left, as suggested in the year 1928 by the "Technischer Aussehuss für Brillenoptik" and which is commonly used for lens prescriptions. Herein, the azimuthal angle is measured in the plane which is orthogonal to the major visual direction or orthogonal to the direction of gaze when viewing in the straight horizontal direction. By using such combination of horizontal and vertical eye movements between the different directions of gaze at which measurements are performed, an improved numerical stability of the data processing in the subsequent analysis of the measurement data can be achieved, such that an increased accuracy of the final result can be achieved.

According to further exemplary embodiments, the direction of gaze, in the primary orientation is orthogonal to a plane including the axes of rotation for rotational movement of the eye according to Listing's Law. This plane is also referred to as Listing's Plane.

The calculating of the shape of one or both surfaces of the spectacle lens may comprise a simulation of light rays traversing the spectacle lens and the eye at a plurality of different directions of gaze of the eye. Herein, the shape of the one or of both surfaces of the spectacle lens can be calculated such that a distribution of resulting aberrations for different directions of gaze corresponds to a desired distribution of aberrations.

Within such simulation, the refraction of the eye can be simulated for a plurality of different directions of gaze such that the axis direction of the astigmatic correction is determined based on the directions of gaze according to Listing's Law. In particular, the refraction of the eye can be simulated for the plurality of directions of gaze such that the cylindrical power of the astigmatic correction is constant for the plurality of directions of gaze and such that only the axis direction of the astigmatism is varied according to Listing's Law for the plurality of directions of gaze. Herein, a constant value of the spherical correction can be used for the various directions of gaze, if a single vision lens is to be manufactured.

When manufacturing a multi-vision lens providing an addition, different spherical powers can be provided for different directions of gaze, and, in particular, for directions of gaze differing in the vertical direction. Moreover, different astigmatic powers can be provided for different directions of gaze. In a multi-vision lens, astigmatic aberrations occur due to the law of Minkwitz such that there is, for at least some directions of gaze, a difference between the astigmatic effect of the spectacle lens required for correcting the deficiency of the eye and the astigmatic effect which can be provided by the spectacle lens. Such astigmatic aberrations can be, to some extent, distributed within the field of view of the wearer of the spectacle lens such that they disturb the viewing experience to only a minor extent. Eye lens manufacturers typically develop distributions of astigmatic aberrations within the field of view which are optimized for specific wearing conditions, such as reading, working at a computer screen or driving a vehicle. Within the simulation, the refraction of the eye can be simulated for the plurality of different directions of gaze, and the shape of the spectacle lens can be calculated such that the axis direction and astigmatic power achieved by the spectacle lens for the different directions of gaze correspond to the predetermined distribution of astigmatic aberrations when Listing's Law and the desired astigmatic correction are taken into account.

According to exemplary embodiments, deviations from Listing's Law can be taken into account, such as deviations which occur upon convergence when viewing an object close to the eye. It has been found that the movements of the eyes correspond very well with Listing's Law if far distance objects are viewed, while deviations from Listing's Law may occur when close objects are viewed.

The determining of the position of the spectacle lens relative to the eye may be performed based on a geometry of a spectacle frame selected by the customer.

The method of manufacturing of the spectacle lens may comprise machining of both surfaces of the spectacle lens according to the determined shape, wherein the shapes of one or both surfaces are calculated according to the methods illustrated above. The calculating of the shape of the surface may in particular include parameters such as an interocular distance of the eyes of the customer and/or an orientation of the spectacle lens relative to the eye and/or a distance of the spectacle lens from the eye.

Moreover, further parameters, such as a required distance and orientation between the front surface and the back surface of the lens based on a prismatic power according to a prescription can be considered.

According to exemplary embodiments, the method is used in the manufacture of spectacle lenses providing an astigmatic correction having a cylindrical power of more than 0.75 diopters, more than 1,00 diopters, more than. 1.50 diopters or more than 2.00 diopters.

The invention further provides spectacles having a spectacle frame and two spectacle lenses mounted on the spectacle frames, wherein the spectacle lenses are manufactured according to the methods illustrated above.

Further embodiments of the invention, provide a computer readable medium or carrier storing information representing a computer program configured to instruct an optical system to perform the methods illustrated above. The computer readable medium or carrier may comprise any medium capable of storing and/or transporting information representing a computer program. Accordingly, the computer readable medium may, for example, include a solid state memory, a magnetic memory, an optical memory or other type of memory. Further, it may include modulated waves and signals carrying information, such as, for example, waves and signals modulated at radio frequencies or higher or lower frequencies and which are suited for transmission across a network, such, as the internet.

Some of the steps of the methods may require user interaction. For example, the measuring of the axis direction of the astigmatism for a particular direction of gaze may require the user to assume a particular direction of gaze upon a request from the system, such that the system can measure the axis direction in the assumed direction of gaze and output corresponding data. Moreover, an operator may be required to mount a lens blank on a, manufacturing tool comprised by the system such that the manufacturing tool may process the lens blank in order to manufacture the lens. For this purpose, the manufacturing tool is controlled by control signals supplied by the system.

BRIEF DESCRIPTION OF THE DRAWINGS

The invention will now be described with reference to the drawings wherein.

DESCRIPTION OF THE PREFERRED
EMBODIMENTS OF THE INVENTION

In the exemplary embodiments described below, components that are alike in function and structure are designated as far as possible by alike reference numerals. Therefore, to understand the features of the individual components of a specific embodiment, the descriptions of other embodiments and of the summary of the disclosure should be referred to.

Figure 1:
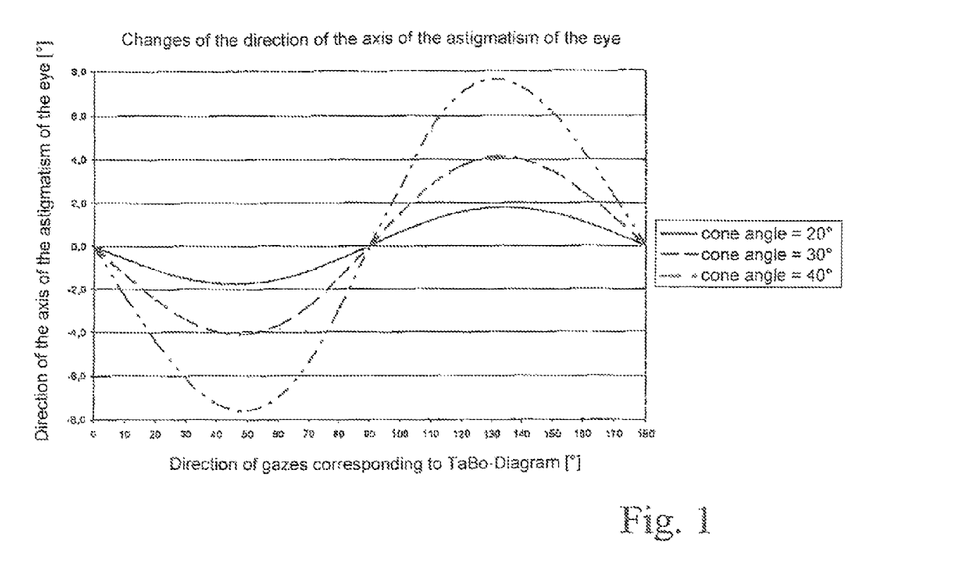
FIG. 1 shows a diagram for illustrating Listing's Law.

FIG. 1 is a schematic illustration of an effect of Listing's Law on the axis direction of an astigmatism for different directions of gaze or viewing directions. For the purposes of this illustration it is assumed that the astigmatism of the eye has an axis direction of 0° in the primary orientation according to Listing's Law. The lines in FIG. 1 are graphs showing the axis direction in dependence on an azimuthal angle of the direction of gaze. For a right eye, an azimuthal angle of 0° corresponds to viewing towards the nose, 90° corresponds to upward viewing, 180° corresponds to viewing in a temporal direction, opposite to the nose. The lines differ with respect to a cone angle, that is, an angle between the direction of gaze in the primary orientation and the direction of gaze in which the axis orientation is measured. The cone angles are 20°, 30° and 40°, respectively, for the three graphs shown in FIG. 1. The ordinate represents the axis direction of the astigmatism in degrees, and the abscissa represents the azimuthal angle in degrees, wherein the nomenclature according to the TaBo-diagram is used in which 0° corresponds to viewing towards the nose for a right eye and 90° corresponds to viewing in the upward direction. The axis directions of the eye are determined relative to a plane orthogonal to the respective direction of gaze. FIG. 1 in particular illustrates the increase of the deviation of the axis direction of the eye with increasing cone angle.

For the application of Listing's Law it Is sufficient to assume that the eye rotates about a point-shaped center of rotation within the eye. It is, however, also possible to assume that various points of rotations of the eye for various possible rotations are distributed within an extended spherical region of the eye. A correct determination of the axis direction of the astigmatism of the eye for each direction of gaze is required for an optimal correction of the astigmatism of the eye using a spectacle lens. The axis direction for each direction of gaze can be determined using Listing's Law which should be applied correctly. Listing's Law includes a primary orientation of the eye which is the basis for the determination of all possible orientation assumed by the eye when viewing in the possible directions of gaze.

Single vision lenses for far side correction are often designed such that the optical axis of a lens having no prismatic power traverses the point of rotation of the eye. The optical axis of such a lens is an axis along which a light ray propagates which is not refracted by the lens. The lens is mounted relative to the eye such that the optical axis of the lens coincides with the major visual direction for viewing on distant objects, wherein the major visual direction is typically 5° to 10° below the horizontal direction of gaze. Single vision lenses having prismatic power are often mounted such that a light ray originating from the rotational center of the eye and propagating in the major visible direction is orthogonal to the front surface of the lens. If no other data are available, the primary orientation of the eye for applying Listing's Law can be set equal to this major visual direction such that it is assumed that the primary orientation of Listing's Law is oriented 5° to 10° below the horizontal direction.

Progressive power lenses are typically mounted on the spectacle frame such that a centration marking provided on the front surface of the spectacle lens coincides with the horizontal straight direction of gaze. This direction is also referred to as the straight ahead gaze direction of the eye. Since the primary orientation of the eye for the application of Listing's Law is assumed with a minimum tension of the eye muscles which is, at first, not dependent from an orientation of the head, it can not be generally assumed that the direction of gaze in the primary orientation corresponds to a direction of gaze fixed in space. In particular, it is not necessary that the primary orientation of the eye is equal to the straight ahead gaze direction assumed for progressive power lenses. If the straight ahead gaze direction of the eye were to coincide with the primary orientation of the eye, the vertical direction would be parallel to Listing's plane.

Figure 2:
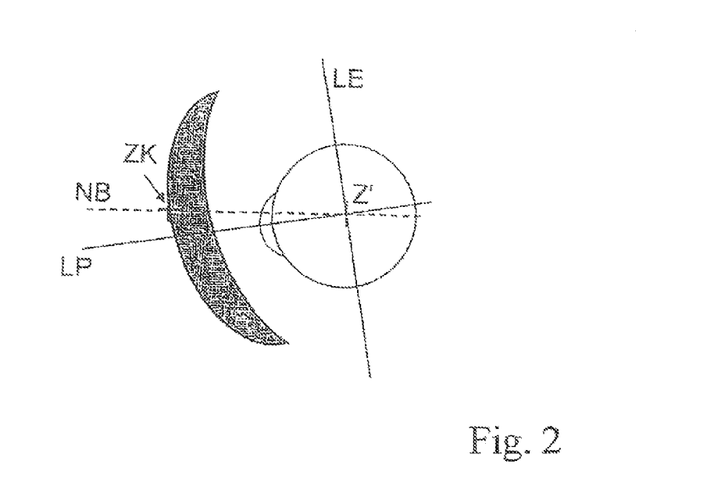
FIG. 2 is a schematic sectional view of an eye and a spectacle lens positioned in front of the eye; and, FIG. 3 is a flowchart illustrating an embodiment of the method.

FIG. 2 is a schematic illustration showing a section through an eye and a spectacle lens mounted in front of the eye. In FIG. 2, Z' designates the center of rotation of the eye, ZK designates the centration marking on the front surface of the lens, wherein the spectacle lens is positioned relative to the eye such that the straight ahead gaze direction NB intersects the centration marking ZK. The eye shown in FIG. 2 is in the primary orientation according to Listing's Law in which the primary direction LP according to Listing's Law is oriented downwards relative to the straight ahead gaze direction NB. Listing's plane LP is oriented orthogonal to the direction LP.

The primary orientation according to Listing's Law can be determined by measuring the astigmatic axis direction for a plurality of orientations. The table below illustrates exemplary measurements obtained from a right eye of a customer:

|  | horizontal viewing angle | vertical viewing angle | measured axis direction |
|---|---|---|---|
| 1. measurement | 0° | 7° downwards | 30° |
| 2. measurement | 10° leftwards | 25° upwards | 25° |
| 3. measurement | 30° rightwards | 5° upwards | 33° |
| 4. measurement | 25° leftwards | 10° upwards | 25° |

Vectors representing the viewing directions indicated in the above table can be defined based on the horizontal and vertical viewing angles indicated in the table as follows: The vector corresponding to the straight ahead gaze direction is first rotated by the indicated vertical viewing angle, and the resulting vector is then rotated by the horizontal viewing angle indicated in the table. This corresponds to first making a vertical eye movement by the indicated viewing angle and then making a horizontal eye movement by the indicated horizontal viewing angle. The axis direction of the astigmatism of the eye was determined relative to the plane orthogonal to the respective direction of gaze, wherein an axis direction of 0° corresponds to a horizontal direction in space of the axis of the astigmatism of the eye.

Starting from an orthogonal, right-handed coordinate system having its positive X-axis direction in the horizontal temporal direction, its positive Y-axis direction in the upward vertical direction and the positive Z-axis direction opposite to the straight ahead gaze direction, the assumed primary orientation of the eye will be defined by the new negative Z-direction of a coordinate system resulting from a rotation of the initial coordinate system about the orthogonal Y-axis by a horizontal angle $\phi_{hor}$ and subsequently a rotation about the X-axis of the resulting system by a vertical angle $\phi_{ver}$. This resulting coordinate system is attached to the primary orientation of the eye.

The measured axis directions of the table can be transformed into this coordinate system. If one assumes an axis direction Ach1 of the eye in the primary orientation of the eye, the axis directions AL1, AL2, AL3, and AL4 of the eye in the transformed directions of gaze can be calculated using Listing's Rule.

Starting from the primary orientation defined by the angles $\phi_{hor}$ and $\phi_{ver}$ and assuming an axis direction Ach1 in the primary orientation, an error F can be defined using the measured axis directions from the above table:

$$F(\phi_{hor}, \phi_{ver}, Ach1) = (AL1-30)^2 + (AL2-25)^2 + (AL3-33)^2 + (AL4-25)^2$$

A minimum of the error function F can be determined using an optimizing method by varying the parameters $\phi_{hor}$, $\phi_{ver}$, an Ach1. For this purpose, the commercially available software MATLAB can be used, for example.

Using such method, the data indicated in the above table results in a primary orientation of the eye at $\phi_{hor}$=5.3° to the right, $\phi_{ver}$=9.0° downward and an axis orientation Ach1=30.1° for the coordinate system attached to the primary orientation of the eye as defined above.

In the above example, measurements of the axis direction are performed at four different eye orientations. A minimum number of necessary different eye orientations is three; more than three measurements can be taken, for example, in order to improve the measurement accuracy or to provide some redundancy.

The direction of the axis of the astigmatism of the eye can be measured at any given direction of gaze using a refraction measurement. Plural refraction measurements can be performed for the plural different directions of gaze. It is also possible to measure the direction of the axis of the astigmatism at each of the plural different directions of gaze by determining a topology of the cornea of the eye at each of the plural directions of gaze. The topology or three dimensional shape of the surface of the cornea can be determined using measurement tools, such as a keratometer, and the measured topology can be transformed into a mathematical representation. A correspondence between the direction of the axis of the astigmatism and the mathematical representation of the cornea can be determined for each of the plural directions of gaze, since the shape of the cornea is generally not a spherical shape, which in particular holds for astigmatic eyes. When the direction of the axis of the astigmatism is known for one particular orientation of the eye, the direction of the astigmatism can be determined for other directions of gaze based on the measurements of the topology of the cornea measured in the other directions of gaze.

Another method of determining the directions of the axis of the astigmatism for plural different directions of gaze involves determining the direction of the axis for one particular direction of gaze, such as the straight ahead gaze direction, by a measurement, such as a refraction measurement. Subsequently, images of the eye recorded by a camera at different directions of gaze are analyzed in order to identify positions and/or shapes of characteristic elements of the eye. The characteristic elements may include, for example, blood vessels within the cornea or a pattern of the iris of the eye. The orientation of the eye can be determined for the different directions of gaze by such image processing, accordingly. A correspondence between the direction of the axis of the astigmatism and the characteristic elements of the eye can be determined. By determining the orientation of the characteristic elements of the eye, the direction of the axis of the astigmatism can be determined for each of the different directions of gaze using this correspondence.

As soon as the primary orientation according to Listing's Rule is known for the eye, the plane according to Listing's Rude can be determined, wherein all axes of rotation of the eye which are necessary to rotate the eye from the primary orientation to the orientation corresponding to a particular direction of gaze coincide with this plane. It is then possible to predict the direction of the axis of the astigmatism for each possible direction of gaze and to calculate local astigmatic powers of the spectacle lens required to compensate the astigmatism of the eye for all possible directions of gaze. It is then possible to use an optimizing method for calculating the shape of one surface or the shapes of both surfaces of the spectacle lens such that the spectacle lens fulfils the requirements of compensating the eye astigmatism for all possible directions of gaze as far as possible. For this purpose, ray bundles traversing the eye and the spectacle lens can be simulated using ray tracing software. For this purpose, it is advantageous to know the exact or expected position of the spectacle lens relative to the eye. This expected position of the spectacle lens relative to the eye can be determined when the customer has selected a desired spectacle frame, before the optimizing method is applied, wherein the optician determines parameters characterizing the position of the spectacle lens relative to the eye. Such parameters may include, for example, a distance of the spectacle frame or lens from the eye, the pantoscopic angle of the spectacle frame at the straight ahead gaze direction, and the phase form angle.

Based on the directions of the axis of the astigmatism of the eye which can be correctly calculated for viewing distant objects in different directions of gaze based on Listing's Rule, it is further possible to take deviations from Listing's Rule into account which may occur by convergence movements of the eye when close objects are viewed. This can be achieved by determining the visual point at which a line of gaze at a particular direction of gaze intersects the back surface of the spectacle lens and a corresponding object distance for which the spectacle lens is designed for the given direction of gaze. It is then possible to determine a change of the direction of the axis of the astigmatism and, if necessary, a change of the cylindrical power resulting from the convergence movement based on such object distance and to add such change of the direction of the axis to the direction of the axis as determined based on Listing's rule.

Figure 3:
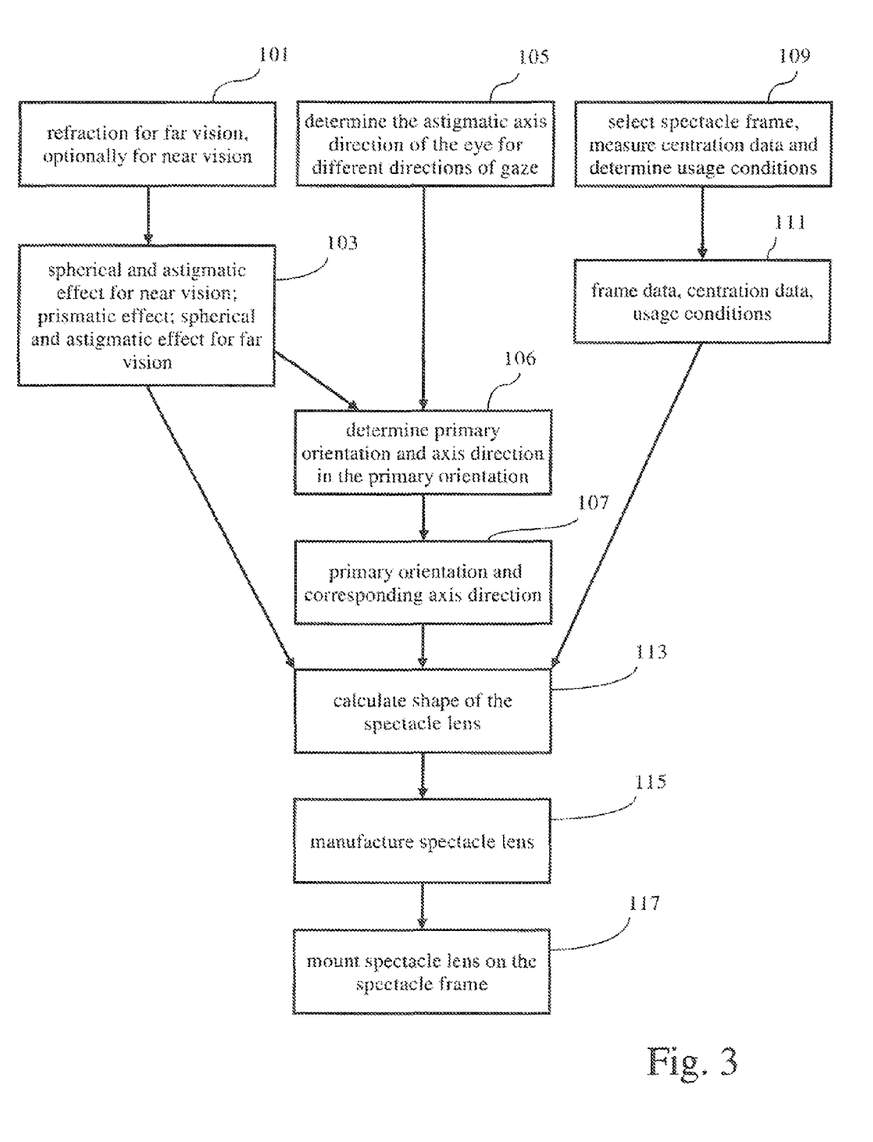

The methods illustrated above are further illustrated with reference to the flowchart of FIG. 3 below. A refraction measurement is performed in a step 101. The refraction measurement, is performed at the eye when viewing a distant object. If desired the refraction measurement can also be performed on the eye when viewing a close object. The refraction measurement is typically performed by an ophthalmologist or an optician. Prescription data are determined based on the refraction measurement. The prescription data represent the optical effect of the spectacle lens required for compensating the ametropea. These data 103 include at least the spheric power and the astigmatic effect, and they may also include a prismatic power and the addition of a multi focal lens or the spheric and astigmatic effect for viewing close objects.

The direction of the axis of the astigmatism of the eye is determined for plural different viewing directions in a step 105. The directions of the axis of the astigmatism can be directly measured using refraction measurements, or they can be indirectly determined based on measurements of a topology of the cornea or from measurements of positions and/or shapes of characteristic elements of the eye. The primary orientation according to Listing's rule is determined in a step 106 based on the directions of the axis of the astigmatism for the different viewing directions and, if desired, based on the direction of the axis of the astigmatism occurring at the refraction measurement in step 101. The direction of the axis of the astigmatism in the primary orientation is then determined in step 107.

The customer selects a desired spectacle frame and lens material in a step 109. Centration data determining the position of the future spectacle lens relative to the frame can be determined based on the selected spectacle frame. Further, the required site of the spectacle lens, the interpupillary distance and the shape of the frame can be determined in step 111. Further data representing usage conditions, such as the position of the spectacle lens relative to the eye and relative to viewed objects, such as the vertex distance, the pantoscopic angle, the phase form, angle, object distances can be determined. Moreover, positions and extensions of far vision regions and near vision regions of a lens can be determined for multi vision lenses.

The steps 101, 105 and 109 can be performed in any desirable order. However, the result of the refraction measurement in step 101 may limit the selection of possible spectacle frames in step 109 based on a static consideration. Therefore, in practice, step 109 will be performed after step 101. The data 103, 107 and 111 obtained in steps 101, 106 and 109 form the basis for the calculating of the shape of the spectacle lens and of optimizing of the shape of the optical lens with respect to remaining aberrations and with respect to aesthetic considerations and weight and thickness requirements in a step 113 in which, the shape of the surfaces of the lens are calculated. The spectacle lens is manufactured, in a step 105 according to the shape determined in step 113. In a step 117, the lens is cut corresponding to the shape of the spectacle frame and mounted on the frame in order to provide the spectacles including the frame and the lenses.

In a further embodiment, the measurement of the direction of the axis of the astigmatism is measured, in step 105 for a greater number of viewing directions. This greater number is, in particular, greater than three and the different viewing directions are selected such that the directions of the axis of the astigmatism used in the simulation of step 113 are determined by interpolation rather than by applying Listing's rule. In such embodiment, it is not necessary to perform steps 106 and 107 for determining the primary orientation of the eye according to Listing's rule and the direction of the axis in this primary orientation.

It is understood that the foregoing description Is that of the preferred embodiments of the invent ion and that various changes and modifications may be made thereto without departing from the spirit and scope of the invention, as defined in the appended claims.

What is claimed is:

1. A method of making a spectacle lens providing at least an astigmatic correction, wherein the method comprises the steps of:
    measuring a direction of an axis of an astigmatism of an eye for each of at least three different directions of gaze of the eye;
    individually determining a position of the spectacle lens relative to the eye; and,
    computing a shape of a surface of the spectacle lens based on the individually determined position of the spectacle lens relative to the eye and the at least three measured directions of the axis of the astigmatism.

2. The method according to claim 1, wherein the measuring of the direction of the axis of the astigmatism of the eye is performed for more than 15 different directions of gaze,
    wherein the calculating of the shape of the surface of the spectacle lens includes a simulation of light rays traversing the eye and the spectacle lens for a plurality of different directions of gaze of the eye; and,
    wherein the direction of the astigmatism of the eye for the plurality of different directions of gaze is determined by interpolation of the measured directions of the axis.

3. The method according to claim 1, further comprising determining a primary orientation of the eye based on the at least three measured directions of the axis of the astigmatism, wherein the shape of the surface of the spectacle lens is calculated based on the individually determined position of the spectacle lens relative to the eye and by applying Listing's Law based on the determined primary orientation of the eye.

4. The method according to claim 3, wherein the calculating of the shape of the surface of the spectacle lens includes a simulation of light rays traversing the eye and the spectacle lens for a plurality of different directions of gaze of the eye, and wherein, in the simulation, directions of the axis of the astigmatism of the eye are calculated for the plurality of directions of gaze by applying Listing's Law based on the individually determined primary orientation.

5. The method according to claim 3, wherein at least two of the at least three different directions of gaze differ by more than 25° in a vertical direction relative to the eye.

6. The method according to claim 3, wherein at least two of the at least three different directions of gaze differ by more than 25° in a horizontal direction relative to the eye.

7. The method according to claim 3, wherein at least two of the at least three directions of gaze are situated in an azimuthal direction about a straight direction of gaze outside of an angular range of ±10° from a vertical direction and outside of an angular range of ±10° from a horizontal direction.

8. The method according to claim 3, wherein the direction of gaze in the primary orientation is orthogonal to a plane including the axes of rotation for rotational movement of the eye according to Listing's Law.

9. The method according to claim 1, wherein the computing of the shape of the surface of the spectacle lens includes an optimization of a distribution of remaining aberrations for different directions of gaze.

10. The method according to claim 1, wherein deviations of orientations of the eye from Listing's Law occurring due to a convergence of the eye when viewing on a close object are considered.

11. The method according to claim 1, wherein a refraction of the eye is simulated for the plurality of different directions of gaze such that a cylindrical power of the astigmatic correction is constant for the different directions of gaze.

12. The method according to claim 1, wherein a refraction of the eye is simulated for the plurality of different directions of gaze such that a spherical power of a spherical correction is constant for the different directions of gaze.

13. The method according to claim 1, wherein a distance of an object from the eye is simulated for the plurality of different directions of gaze such that the distance for downward directions of gaze is smaller than the distance for horizontal directions of gaze or upward directions of gaze.

14. The method according to claim 1, wherein the shape of the surface of the spectacle lens is calculated such that the spectacle lens provides spherical powers which are smaller for upward directions of gaze than for downward directions of gaze.

15. The method according to claim 1, wherein the determining of the position of the spectacle lens relative to the eye is determined based on a geometry of a selected spectacle frame.

16. The method according to claim 1, further comprising shaping the surface of the spectacle lens according to the calculated shape of the surface.

17. Spectacles for a first and a second eye of a wearer, at least the first eye having an astigmatism, the astigmatism defining an axis with a direction measured in at least three different directions of gaze of the first eye, the spectacles comprising:
a spectacle frame;
a first spectacle lens mounted on said spectacle frame so as to correspond to the first eye of the wearer;
a second spectacle lens mounted on said spectacle frame so as to correspond to the second eye of the wearer;
said first spectacle lens having an individually determined position relative to the first eye; and,
said first spectacle lens defining a surface having a computed shape based on the individually determined position of the first spectacle lens relative to the first eye and the at least three measured directions of the axis of the astigmatism.

18. A computer readable medium storing information representing a computer program configured to instruct an optical system to perform a method comprising:
measuring a direction of an axis of an astigmatism of an eye for each of at least three different directions of gaze of the eye;
individually determining a position of the spectacle lens relative to the eye; and,
computing a shape of a surface of the spectacle lens based on the individually determined position of the spectacle lens relative to the eye and the at least three measured directions of the axis of the astigmatism.

19. The method according to claim 3, wherein at least two of the at least three different directions of gaze differ by more than 35° in a vertical direction relative to the eye.

20. The method according to claim 3, wherein at least two of the at least three different directions of gaze differ by more than 35° in a horizontal direction relative to the eye.

21. A method of making a spectacle lens providing at least an astigmatic correction, wherein the method comprises the steps of:
measuring a direction of an axis of an astigmatism of an eye for each of at least three different directions of gaze of the eye;
individually determining a position of the spectacle lens relative to the eye; and,
computing a shape of a surface of the spectacle lens based on the individually determined position of the spectacle lens relative to the eye and the at least three measured directions of the axis of the astigmatism,
wherein the measuring of the direction of the axis of the astigmatism of the eye is performed for more than 30 different directions of gaze;
wherein the calculating of the shape of the surface of the spectacle lens includes a simulation of light rays traversing the eye and the spectacle lens for a plurality of different directions of gaze of the eye; and,
wherein the direction of the astigmatism of the eye for the plurality of different directions of gaze is determined by interpolation of the measured directions of the axis.

22. A method of making a spectacle lens providing at least an astigmatic correction, wherein the method comprises the steps of:
measuring a direction of an axis of an astigmatism of an eye for each of at least three different directions of gaze of the eye;
individually determining a position of the spectacle lens relative to the eye; and,
computing a shape of a surface of the spectacle lens based on the individually determined position of the spectacle lens relative to the eye and the at least three measured directions of the axis of the astigmatism,
wherein the measuring of the direction of the axis of the astigmatism of the eye is performed for more than 60 different directions of gaze;
wherein the calculating of the shape of the surface of the spectacle lens includes a simulation of light rays traversing the eye and the spectacle lens for a plurality of different directions of gaze of the eye; and, wherein the direction of the astigmatism of the eye for the plurality of different directions of gaze is determined by interpolation of the measured directions of the axis.

23. A method of making a spectacle lens providing at least an astigmatic correction, wherein the method comprises the steps of:
    measuring a direction of an axis of an astigmatism of an eye for each of at least three different directions of gaze of the eye;
    individually determining a position of the spectacle lens relative to the eye; and,
    computing a shape of a surface of the spectacle lens based on the individually determined position of the spectacle lens relative to the eye and the at least three measured directions of the axis of the astigmatism;
    wherein the measuring of the direction of the axis of the astigmatism of the eye is performed for more than 15 different directions of gaze,
    wherein the calculating of the shape of the surface of the spectacle lens includes a simulation of light rays traversing the eye and the spectacle lens for a plurality of different directions of gaze of the eye; and,
    wherein the direction of the astigmatism of the eye for the plurality of different directions of gaze is determined by interpolation of the measured directions of the axis.

24. A method of making a spectacle lens providing at least an astigmatic correction, wherein the method comprises the steps of:
    measuring a direction of an axis of an astigmatism of an eye for each of at least three different directions of gaze of the eye;
    individually determining a position of the spectacle lens relative to the eye;
    computing a shape of a surface of the spectacle lens based on the individually determined position of the spectacle lens relative to the eye and the at least three measured directions of the axis of the astigmatism; and,
    determining a primary orientation of the eye based on the at least three measured directions of the axis of the astigmatism, wherein the shape of the surface of the spectacle lens is calculated based on the individually determined position of the spectacle lens relative to the eye and by applying Listing's Law based on the determined primary orientation of the eye.

25. A method of making a spectacle lens providing at least an astigmatic correction, wherein the method comprises the steps of:
    measuring a direction of an axis of an astigmatism of an eye for each of at least three different directions of gaze of the eye;
    individually determining a position of the spectacle lens relative to the eye; and,
    computing a shape of a surface of the spectacle lens based on the individually determined position of the spectacle lens relative to the eye and the at least three measured directions of the axis of the astigmatism;
    wherein the calculating of the shape of the surface of the spectacle lens includes a simulation of light rays traversing the eye and the spectacle lens for a plurality of different directions of gaze of the eye; and,
    wherein the direction of the astigmatism of the eye for the plurality of different directions of gaze is determined by interpolation of the measured directions of the axis.

26. Spectacles for a first and a second eye of a wearer, at least the first eye having an astigmatism, the astigmatism defining an axis with a direction measured in at least three different directions of gaze of the first eye, the spectacles comprising:
    a spectacle frame;
    a first spectacle lens mounted on said spectacle frame so as to correspond to the first eye of the wearer;
    a second spectacle lens mounted on said spectacle frame so as to correspond to the second eye of the wearer;
    said first spectacle lens having an individually determined position relative to the first eye; and,
    said first spectacle lens defining a surface having a computed shape based on the determined position of the first spectacle lens relative to the first eye and the at least three measured directions of the axis of the astigmatism,
    wherein the direction of the axis of the astigmatism of the eye has been measured for more than 15 different directions of gaze,
    wherein the shape of the surface of the spectacle lens has been calculated by including a simulation of light rays traversing the eye and the spectacle lens for a plurality of different directions of gaze of the eye; and,
    wherein the direction of the astigmatism of the eye for the plurality of different directions of gaze has been determined by interpolation of the measured directions of the axis.

27. Spectacles for a first and a second eye of a wearer, at least the first eye having an astigmatism, the astigmatism defining an axis with a direction measured in at least three different directions of gaze of the first eye, the spectacles comprising:
    a spectacle frame;
    a first spectacle lens mounted on said spectacle frame so as to correspond to the first eye of the wearer;
    a second spectacle lens mounted on said spectacle frame so as to correspond to the second eye of the wearer;
    said first spectacle lens having an individually determined position relative to the first eye; and,
    said first spectacle lens defining a surface having a computed shape based on the determined position of the first spectacle lens relative to the first eye and the at least three measured directions of the axis of the astigmatism,
    wherein a primary orientation of the eye has been determined based on the at least three measured directions of the axis of the astigmatism, wherein the shape of the surface of the spectacle lens has been calculated based on the individually determined position of the spectacle lens relative to the eye and by applying Listing's Law based on the determined primary orientation of the eye.

28. Spectacles for a first and a second eye of a wearer, at least the first eye having an astigmatism, the astigmatism defining an axis with a direction measured in at least three different directions of gaze of the first eye, the spectacles comprising:
    a spectacle frame;
    a first spectacle lens mounted on said spectacle frame so as to correspond to the first eye of the wearer;
    a second spectacle lens mounted on said spectacle frame so as to correspond to the second eye of the wearer;
    said first spectacle lens having an individually determined position relative to the first eye; and,
    said first spectacle lens defining a surface having a computed shape based on the individually determined position of the first spectacle lens relative to the first eye and the at least three measured directions of the axis of the astigmatism, wherein the shape of the surface of the spectacle lens has been calculated by including a simulation of light rays traversing the eye and the spectacle lens for a plurality of different directions of gaze of the eye; and, wherein the direction of the astigmatism of the eye for the plurality of different directions of gaze has been determined by interpolation of the measured directions of the axis.

29. The method according to claim 1, further comprising: selecting a spectacle frame, wherein the position of the spectacle lens relative to the eye is determined based on the selected spectacle frame.

30. The method according to claim 29, wherein the determining of the position of the spectacle lens relative to the eye includes at least one of determining a distance of the selected spectacle frame from the eye, and determining of a pantoscopic angle of the selected spectacle frame at the straight ahead gaze direction.

31. The method according to claim 1, wherein the determining of the position of the spectacle lens relative to the eye includes at least one of determining a distance of the spectacle lens from the eye, and determining of a pantoscopic angle of the spectacle lens at the straight ahead gaze direction.

* * * * *

UNITED STATES PATENT AND TRADEMARK OFFICE
CERTIFICATE OF CORRECTION

PATENT NO.        : 9,459,468 B2
APPLICATION NO.   : 13/901270
DATED             : October 4, 2016
INVENTOR(S)       : Helmut Wietschorke Page 1 of 1

It is certified that error appears in the above-identified patent and that said Letters Patent is hereby corrected as shown below:

In the Specification

In Column 3:
Line 59: delete "Aussehuss" and substitute -- Ausschuss -- therefor.

In Column 5:
Line 14: delete "1,00" and substitute -- 1.00 -- therefor.
Line 14: delete "than." and substitute -- than -- therefor.
Line 33: delete "such," and substitute -- such -- therefor.
Line 41: delete "a," and substitute -- a -- therefor.

In Column 6:
Line 24: delete "Is" and substitute -- is -- therefor.

In Column 8:
Line 55: delete "Rude" and substitute -- Rule -- therefor.

Signed and Sealed this
Tenth Day of January, 2017

Michelle K. Lee
*Director of the United States Patent and Trademark Office*